United States Patent
Meskens

(10) Patent No.: US 8,923,968 B2
(45) Date of Patent: Dec. 30, 2014

(54) POWER LINK FOR IMPLANTABLE DEVICES

(75) Inventor: Werner Meskens, Opwijk (BE)

(73) Assignee: Cochlear Limited, Macquarie University, NSW (AU)

( * ) Notice: Subject to any disclaimer, the term of this patent is extended or adjusted under 35 U.S.C. 154(b) by 458 days.

(21) Appl. No.: 12/741,009

(22) PCT Filed: Oct. 30, 2008

(86) PCT No.: PCT/AU2008/001608
§ 371 (c)(1),
(2), (4) Date: Aug. 16, 2010

(87) PCT Pub. No.: WO2009/055856
PCT Pub. Date: May 7, 2009

(65) Prior Publication Data
US 2010/0312310 A1    Dec. 9, 2010

(30) Foreign Application Priority Data
Oct. 30, 2007    (AU) ................................ 2007905943

(51) Int. Cl.
*A61N 1/00* (2006.01)
*A61N 1/378* (2006.01)
*H02J 5/00* (2006.01)
*H01F 38/14* (2006.01)

(52) U.S. Cl.
CPC .............. *A61N 1/3787* (2013.01); *H02J 5/005* (2013.01); *H01F 38/14* (2013.01)

USPC .................................. 607/33; 607/36; 607/61

(58) Field of Classification Search
CPC .... A61N 1/3758; A61N 1/0541; A61N 1/375
USPC .................................. 607/33, 32, 36, 61, 60
See application file for complete search history.

(56) References Cited

U.S. PATENT DOCUMENTS

| | | |
|---|---|---|
| 4,038,625 A | 7/1977 | Tompkins et al. |
| 5,741,316 A | 4/1998 | Chen et al. |
| 5,991,664 A | 11/1999 | Seligman |
| 6,067,474 A | 5/2000 | Schulman et al. |
| 2005/0021100 A1 | 1/2005 | Tsukamoto et al. |
| 2005/0288740 A1 | 12/2005 | Hassler et al. |
| 2007/0141887 A1 | 6/2007 | Kuo et al. |
| 2007/0217163 A1 | 9/2007 | Greatbatch et al. |

FOREIGN PATENT DOCUMENTS

| | | |
|---|---|---|
| EP | 1246563 B1 | 2/2005 |
| WO | 2006010013 A1 | 1/2006 |

OTHER PUBLICATIONS

International Search Report. PCT/AU2008/001608. Mailed Dec. 23, 2008.
Written Opinion. PCT/AU2008/001608. Mailed Dec. 23, 2008.

*Primary Examiner* — Michael Kahelin
*Assistant Examiner* — Mallika D Fairchild
(74) *Attorney, Agent, or Firm* — K&L Gates LLP

(57) ABSTRACT

A power transfer system for an implanted device, such as an implanted medical device. The implanted device and a power transfer device each include a coil with a magnetically permeable core, so that operatively the coils are magnetically coupled, so as to improve the efficiency of power transfer. The coil resides in an electrically conductive implant case.

26 Claims, 14 Drawing Sheets

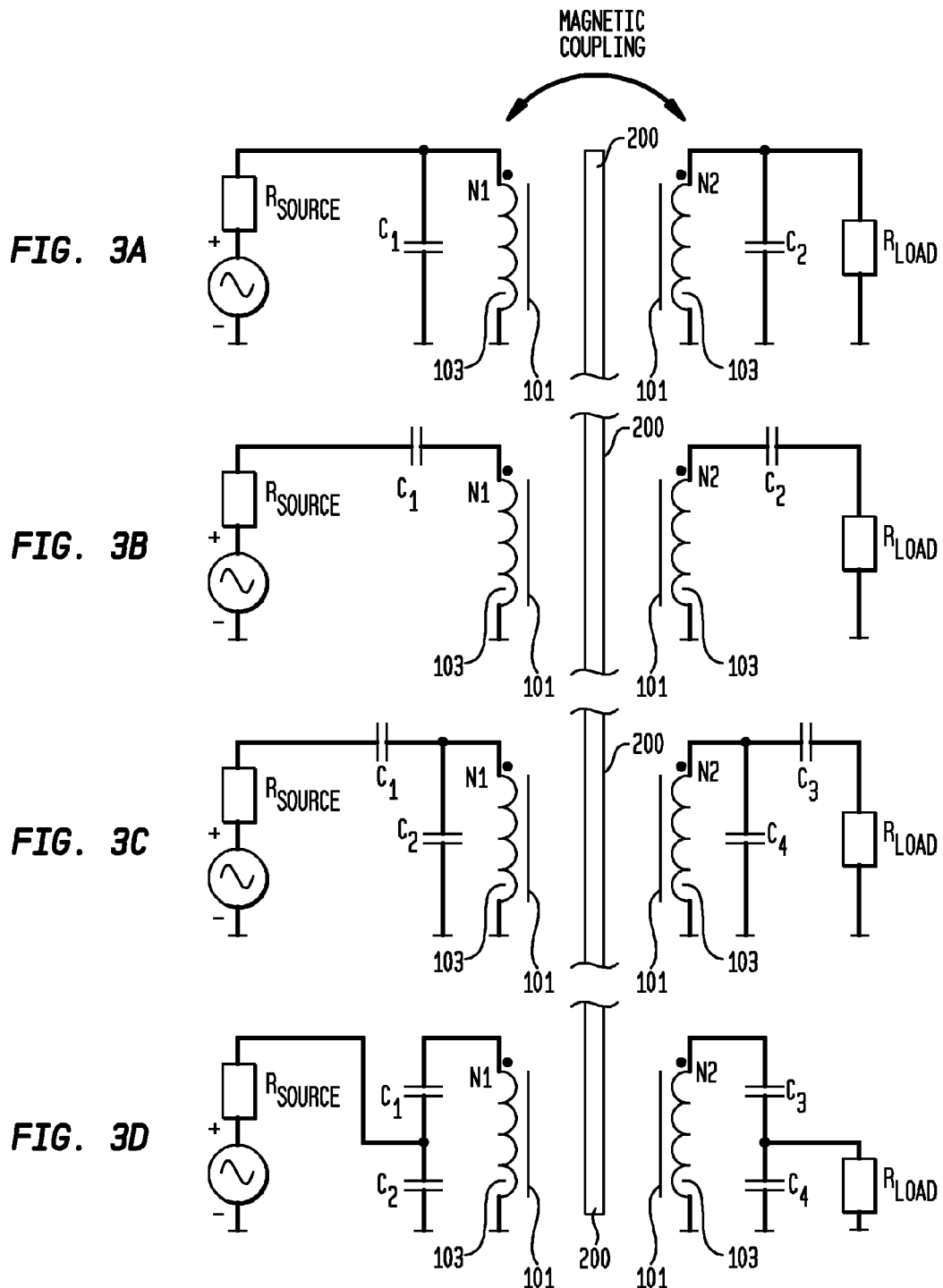

POWER LINK FOR IMPLANTABLE DEVICES

CROSS-REFERENCE TO RELATED APPLICATIONS

This application is a National Stage Application of International Application Number PCT/AU2008/001608, filed Oct. 30, 2008, and which claims the benefit of Australian Provisional Application Number 2007905943, filed Oct. 30, 2007. The contents of these applications are hereby incorporated by reference herein.

BACKGROUND

1. Field of the Invention

The present invention relates generally to implantable medical devices, and more particularly, to a power link for implantable medical devices.

2. Related Art

Many implantable devices have a transcutaneous link to provide continuous or intermittent transfer of electrical power to the implanted device, often from an externally worn battery. The most common form of such a power link uses, two magnetically coupled air coils, typically operating at a frequency in the megahertz range, with the power supplied from an external battery source.

Some implants are constructed from non-conductive materials, for example ceramics, and in this case the implanted coil may be positioned inside the casing. Other implanted devices are housed in metal enclosures, for example formed from titanium or alloys thereof. Titanium is widely used for medical implants since it is inert within the human body, lightweight and strong. Active implantable medical devices (AIMD) such as cochlear implants (CI) generally have reinforced titanium casings.

When an inductive link is arranged to operate across a casing made of titanium or other conductive material, the casing generally operates to shield the incoming power and absorb it, causing an increase of temperature of the casing and hence the contained device. Accordingly, for such devices the implanted air coils have been typically embedded in a flexible biocompatible and electro-magnetically transparent material (e.g. polymers, silicone rubbers), and located external to the casing. As a consequence of improvements in battery technology, the current trend is for implantable devices to include battery capacity, to allow for periods of operation without access to an external power source. This allows for the possibility of totally implanted devices, with clear aesthetic and practical advantages for the users.

SUMMARY

According to a first aspect, of the present invention, there is provided an implantable medical device system, comprising: a first hermetically sealed casing that is at least partially conductive; first and second inductively coupled elements each comprising an inductive coil disposed about a magnetically permeable core; wherein the first element is disposed in the casing, and the second element is disposed external to the casing, and wherein the first and second elements provide transfer of power across the at least partially conductive casing.

According to a second aspect, there is provided a power transfer system for an implantable device system having a first hermetically sealed casing that is at least partially conductive, the power transfer system comprising: first and second inductively coupled elements each comprising an inductive coil disposed about a magnetically permeable core; wherein the first element is disposed in the casing, and the second element is disposed external to the casing, and wherein the first and second elements provide transfer of power across the at least partially conductive casing.

According to a further aspect, there is provided an implantable device, comprising: a hermetically sealed casing that is at least partially conductive; a first element configured to inductively couple with a second element, wherein each of the first and second element comprise an inductive coil disposed about a magnetically permeable core; wherein the first element is disposed in the casing, and the second element is disposed external to the casing, and wherein the first element is configured to inductively couple with the second element to provide transfer of power across the at least partially conductive casing.

BRIEF DESCRIPTION OF THE DRAWINGS

Embodiments of the present invention are described below with reference to the attached drawings, in which:

FIG. 3A illustrates a resonant circuit which may be implemented with magnetically coupled elements, in accordance with an embodiment of the present invention;

FIG. 3B illustrates a resonant circuit which may be implemented with magnetically coupled elements, in accordance with an embodiment of the present invention;

FIG. 3C illustrates a resonant circuit which may be implemented with magnetically coupled elements, in accordance with an embodiment of the present invention;

FIG. 3D illustrates a resonant circuit which may be implemented with magnetically coupled elements, in accordance with an embodiment of the present invention;

DETAILED DESCRIPTION

Aspects of the present invention are generally directed to an implantable medical device system having a conductive casing that encapsulates at least a portion of the system, and two inductively coupled elements, each comprising a magnetically permeable core. These inductively coupled elements may be used to transfer power across the conductive casing. One of the elements is disposed in the casing, while the second element is external to the casing. The elements each comprise an inductive coil disposed about the magnetically permeable core, and provide transfer of power across the conductive casing.

Broadly, an embodiment of the present invention provides an inductive link, wherein the implanted coil includes a magnetically permeable core, and is operable at a relatively low frequency. The link is accordingly relatively efficient, even at low frequencies, and the lower frequency operation reduces the losses in the casing.

The embodiment may permit greater efficiency of power transfer, as well as the option of transfer across a conductive casing. The improved efficiency has advantages for the device relating to battery size, charging time and user convenience. Further, as losses in power transfer appear as heat, unwanted heat generation in the implanted components is minimized.

Deploying a power transfer arrangement according to an embodiment across the titanium or other casing means that no feed through is required to transfer power from the implantable electrical power source device (IEPSD), which reduces manufacturing costs, as well as minimizing the risk of undesired entry or egress of material from the IEPSD. Having a fully sealed casing also minimizes the risk of leakage currents or electrolytic effects.

Embodiments of the present invention are applicable to a wide variety of implantable devices, such as the transfer of power between implanted components, for example from an implanted battery to an AIMD, or for the transfer of power to an AIMD or IEPSD from an external device. Embodiments may be applied to any implantable medical device which requires a power supply, for example hearing prostheses including cochlear implants and hearing aids; monitoring devices of various types; pacers, defibrillators and the like; retinal and other neural stimulators; or powered drug dispensing devices. Embodiments may also be applied to implanted devices which do not perform a medical function.

Whilst the embodiments will be mainly explained with reference to an implantable cochlear implant system, it will be appreciated that this is illustrative, and in no way limitative of the applicability of the present invention.

Figure 1:
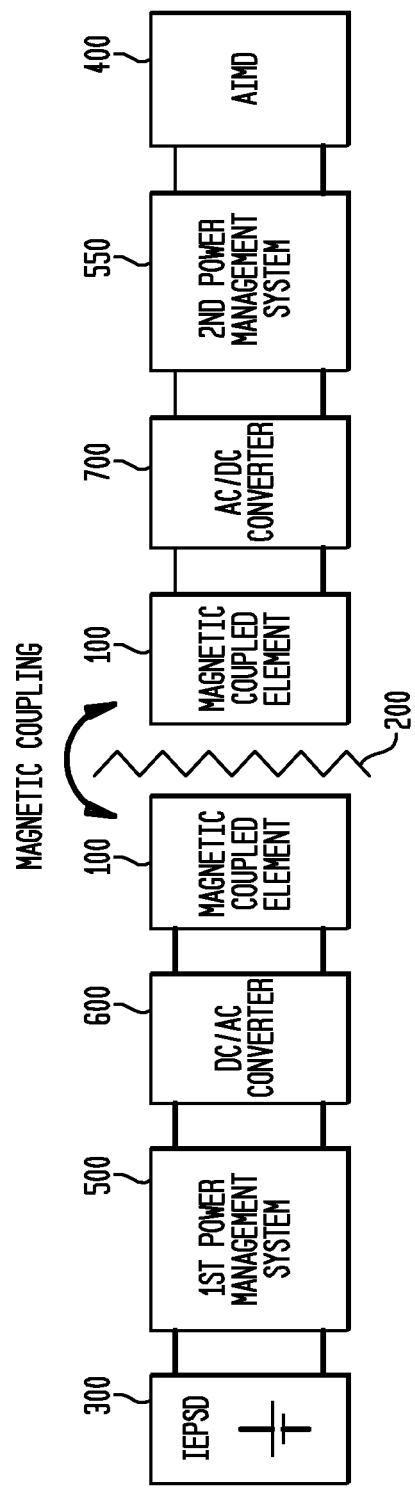
FIG. 1 is a schematic diagram of an embodiment comprising a power link between an implantable electrical power source device (IEPSD) and an active implantable medical device (AIMD), in accordance with an embodiment of the present invention.

FIG. 1 illustrates schematically one implementation of a power link between an active implantable medical device (AIMD) 400 and an implantable electrical power source device (IEPSD) 300. The power link is based on a coupled magnetic field using magnetic coupled elements 100 containing magnetic permeable cores. Power management systems 500, 550 and converters 600, 700 provide optimum adaptation and power transfer between the IEPSD 300 and AIMD 400. The power transfer may be uni-directional or bidirectional (e.g. FIG. 6).

The converters 600, 700 provide conversion for/of alternating electrical signals required for magnetic coupling between the stationary magnetic coupled elements 100.

The IEPSD 300 and AIMD 400 are housed in separate biocompatible casings. It will be understood that it is advantageous to separate the power supply and the active device. For many active devices, the system is very carefully positioned, and it is not desirable to explant unless the device fails. For example, for a cochlear implant, the electrode array will be located within the scala tympani, and the surrounding structures will have healed and grown around it over time. The array will be connected to bone and other tissue, and explantation accordingly risks damage to the nearby auditory structures.

However, the power supply will always have a finite life, and will need to be replaced at some interval. Depending on the implementation, non-magnetic relatively low electrical conductive or non-conductive materials could be used for the casing. Besides human tissue, the separation between the IEPSD 300 and AIMD 400 could consist of biocompatible materials such as titanium, its biocompatible alloys, ceramics or other materials as is known in the art for implanted devices. Using magnetic coupled elements 100 for power transfer between implants is often a better choice then using electrical (often less reliable) connections. Magnetic coupled elements 100 avoid corrosion effects, bad electrical contacts and electrolysis, for example. The second power management system block 550 provides a stabilized supply voltage to the AIMD 400 and controls the AC/DC converter block 700 to obtain maximal power efficiency. Ideally, it can be configured to trigger an alarm by detecting absence of power, low battery voltage status of the IEPSD or any other power link failure.

When the IEPSD 300 is charged through the AIMD 400 from an external body worn charger device 900 (see FIG. 6), the power transfer direction is reversed by both power management system blocks 500 and 550. In this case, the first power management block 500 will regulate adequate current and voltage transfer for charging the IEPSD battery 300.

FIGS. 2A to 2D show alternative detailed constructions of the magnetic coupled elements 100. They each consist of a magnetic permeable core (111, 121, 131, 141), electrical conductive windings 103 and, most often, a capacitor (112, 122, 132, 142) placed in parallel to the primary and secondary windings 103.

Different shapes of cores are available such as half toroids or C-shapes, U- or E-shaped cores and cylindrical cores (rods). The shape of the core determines how easy or difficult it is to do the assembly and to place the windings 103 around the core. The window configuration for the elements 100 may comprise a wide window to maximize winding breadth and minimize the number of layers.

Figure 2:
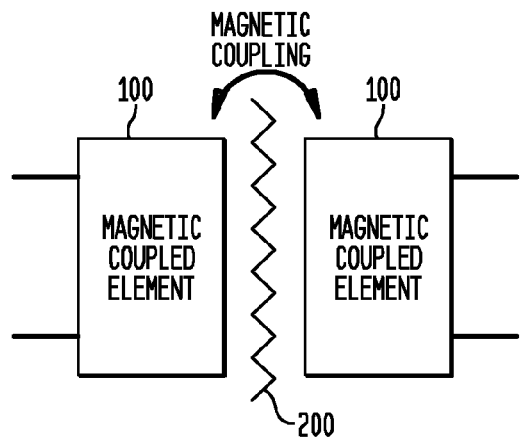
FIG. 2 is a block diagram of the magnetically coupled elements of FIG. 1, in accordance with an embodiment of the present invention.
Figure 2A:
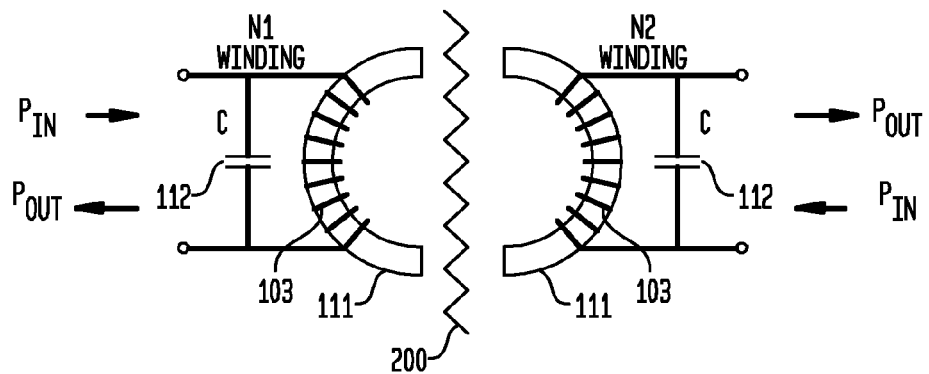
FIG. 2A is a schematic diagram of the magnetically coupled elements of FIG. 1, in accordance with an embodiment of the present invention.
Figure 2B:
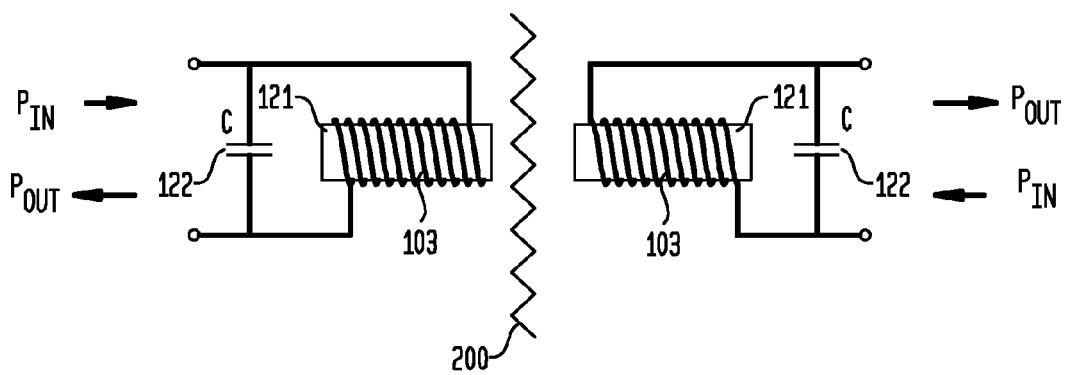
FIG. 2B is schematic diagram of one embodiment of the magnetically coupled elements of FIG. 2, in accordance with an embodiment of the present invention.
Figure 2C:
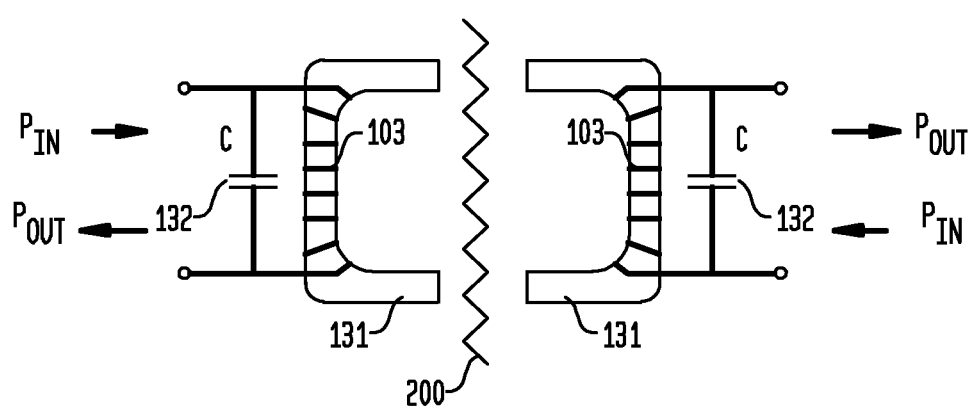
FIG. 2C is a schematic diagram of an alternative embodiment of the magnetically coupled elements of FIG. 1, in accordance with an embodiment of the present invention.
Figure 2D:
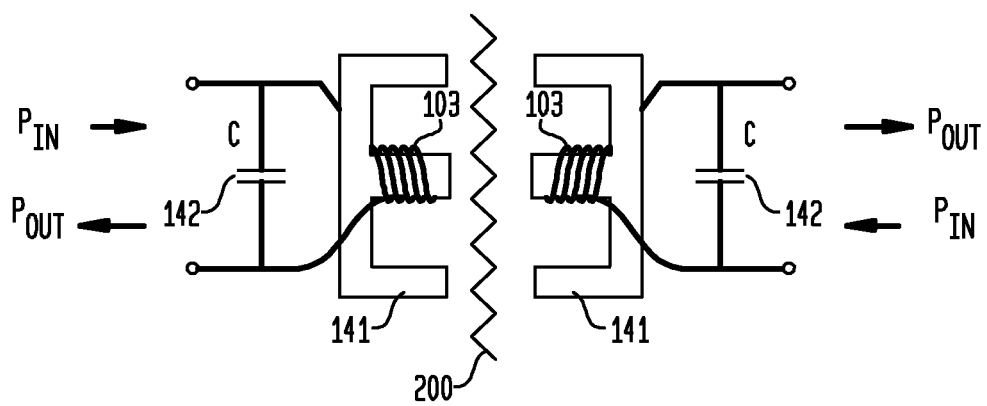
FIG. 2D is a schematic diagram of an alternative embodiment of the magnetically coupled elements of FIG. 1, in accordance with an embodiment of the present invention.

FIG. 2A illustrates a C-shaped core implementation 111 with parallel capacitors 112. FIG. 2B illustrates a rod-shaped implementation 121 with parallel capacitors 122. FIG. 2C illustrates a U-shaped configuration 131; and FIG. 2D illustrates an E-shaped configuration 141.

The core material is selected as appropriate for the desired transformer frequency. The most important core materials are the ferromagnetic materials and ferrimagnetic materials.

Ferromagnetic materials are materials composed from iron (Fe) or iron alloy (Fe with Si, No, Ni, Cr, Cu, Zn . . . ). Soft ferrite is a class of ferrite material based on the spinel or cubic crystal structure. They are produced in two material categories, manganese-zinc (MnZn) and nickel-zinc (NiZn), both in composition with Fe2O3. They are characterized by its high material resistivity. MnZn is primarily used for frequencies less than 2 MHz. NiZn is the choice for operating above 2 MHz up to a few hundred MHz. For a power link through a titanium casing, because of frequency a MnZn soft-ferrite core would preferably be used. As a specific practical example, the outer dimensions of an E-core 141 made of Mn—Zn operating at 30 KHz could be 10millimeters or even smaller to transfer a current of some tens of milliamperes between an IEPSD 300 and AIMD 400.

Power transfer through loosely magnetic coupled elements is not efficient. This is especially the case when the thickness of the casing material 200 is relatively large. For relatively large separations, the magnetic coupled elements 100 could be seen as loosely coupled primary and secondary circuits. Due to relatively small mutual coupling, the windings 103 represent very high inductances or leakage reactances at their respective terminals. From a viewpoint of power efficiency, maximal power transfer is achieved when source and load impedances are complex conjugated to each other.

For a purely resistive load (and source), inductive components of the transformer are preferably cancelled out. If the primary and secondary circuits consist of at least one resonant circuit, adding a series, parallel capacitor or any combination as shown in FIG. 3A to 3D, the power transfer can be optimized.

FIG. 3A to 3D shows various alternative resonant circuits which can be used to assist in impedance matching.

Figure 4:
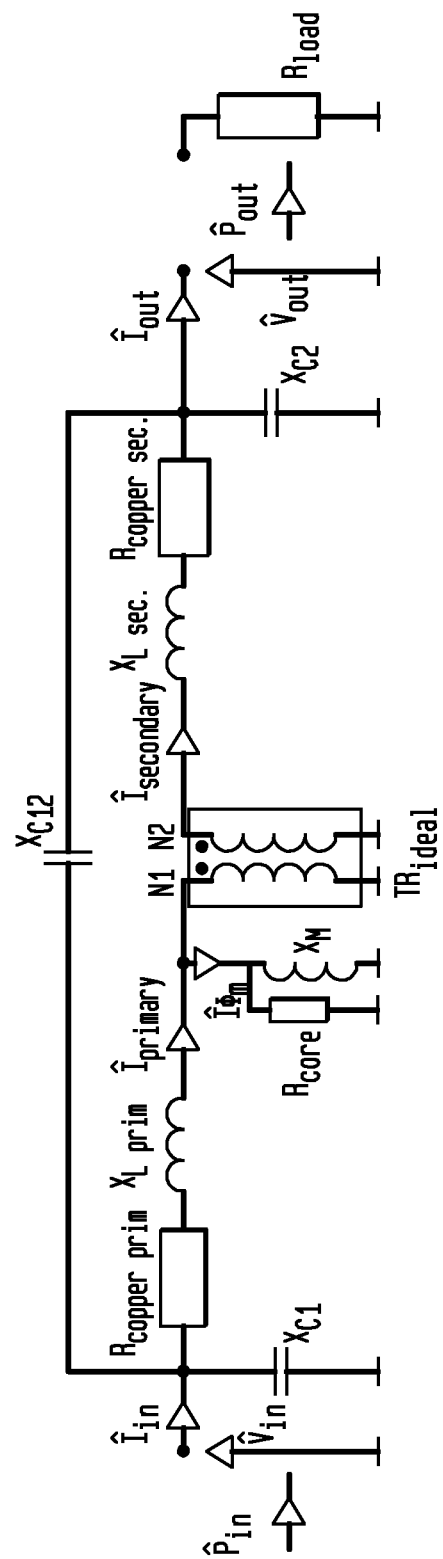
FIG. 4 is schematic drawing of a 'Steinmetz transformer' model.

In general, the higher the loaded or operating Q of the circuit, the smaller the mutual inductance required for the same power transfer. Another aspect of power transfer efficiency is the core and winding losses. Therefore an estimate of power transfer efficiency using the Steinmetz transformer model shown in FIG. 4 is useful.

The total losses of a transformer include the losses in the electric circuit, magnetic circuit, and dielectric circuit (equation 1).

$$P_{totalloss}=P_{electricloss}+P_{magneticloss}+P_{dielectricloss} \quad \text{(Equation 1)}$$

Electric circuit and magnetic circuit losses are the most important losses. Electric circuit losses are also referred as copper losses and they increase with current (I2R). These copper losses are represented as Rcopper in FIG. 4.

Magnetic or core losses are caused by hysteresis and eddy current losses (equation 2). Hysteresis loss is that energy lost by reversing the magnetic field in the core. Eddy current loss is a result of induced currents circulating in the core. Note that copper windings themselves could also be contaminated by eddy-currents.

$$P_{coreloss}=P_{hysteresisloss}+P_{eddycurrentloss} \quad \text{(Equation 2)}$$

The core losses are represented as $R_{core}$ in FIG. 4.

Dielectric losses from insulators are represented by the imaginary part of the dielectric constant $\in r$ and correspond to the leakage resistance. Dielectric losses are often not considered since they are low.

$$P_{totalloss} \approx P_{copperloss}+P_{hysteresisloss}+P_{eddycurrentloss} \quad \text{(Equation 3)}$$

Figure 5:
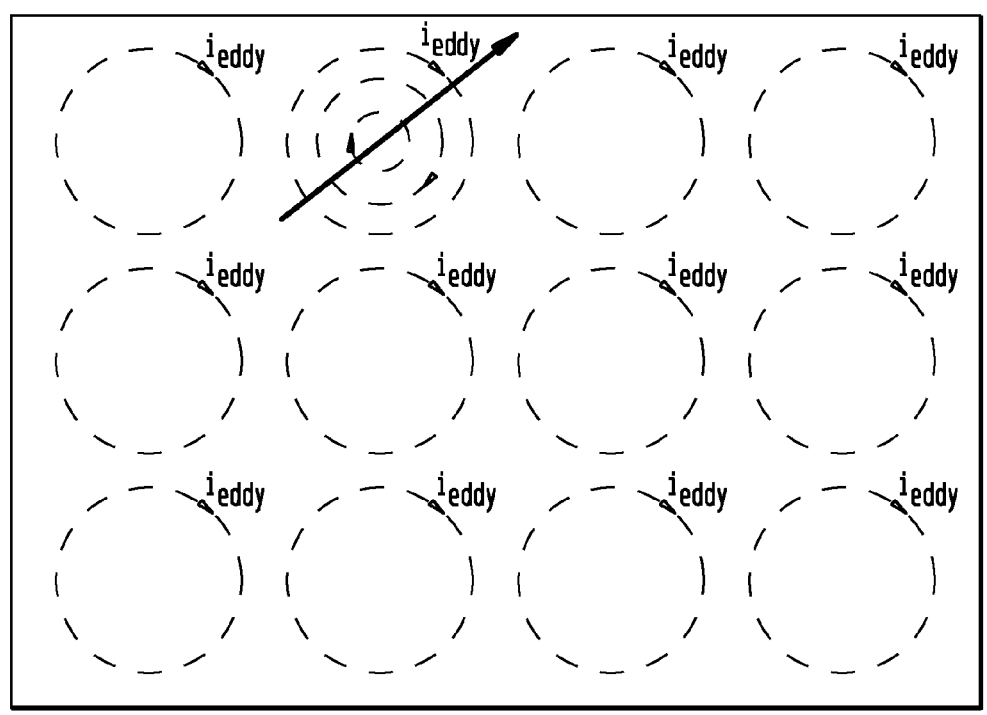
FIG. 5 schematically illustrates eddy currents within a conductive material.

As a last portion that contributes to power transfer efficiency, the losses of the casing material 200 need also to be taken into account. In case of low electrical conductive material such as Titanium, losses are mainly due to eddy currents that are also known as Foucault currents. The stronger the magnetic field intensity (B), and the higher the electrical conductivity of the casing, the greater the current developed and the greater the opposing force. As a result, the eddy currents will heat up the casing material 200. The eddy currents of course themselves operate as electromagnets to induce magnetic fields which oppose the change in the external magnetic field. FIG. 5 illustrates eddy currents within a conductive material.

Since electrical conductivity of the casing material 200 is an important factor for losses, using other biocompatible Titanium alloys with lower electrical conductivities as casing material is likely to enhance the efficiency (e.g. +8% Al). It is anticipated that the casing could be formed of a number of parts of different materials, provided each material exhibits electrically low-conductive characteristics.

Eddy current losses inside electrical low-conductive materials increase as operating frequency increases. Consequently the operating frequency is preferably kept as low as possible. Of course, at too low an operating frequency an increase in the core volume may be required to avoid magnetic field intensity saturation. For a Ti-casing with 500 um thickness, for example, the frequency is preferably below 250 KHz, in order to obtain reasonable power transfer efficiency.

As the frequency decreases, the core size will increase (and data transfer rate decreases too if the link includes modulation.) It will be appreciated that the person skilled in the art can select an appropriate frequency range based upon the material, its thickness, and the required operating characteristics.

The total casing material loss depends also on material thickness and the cross sectional area of the material. Therefore the casing material thickness and cross section area of the magnetic pole shoes of the core are preferably chosen to be as low as possible.

Figure 6:
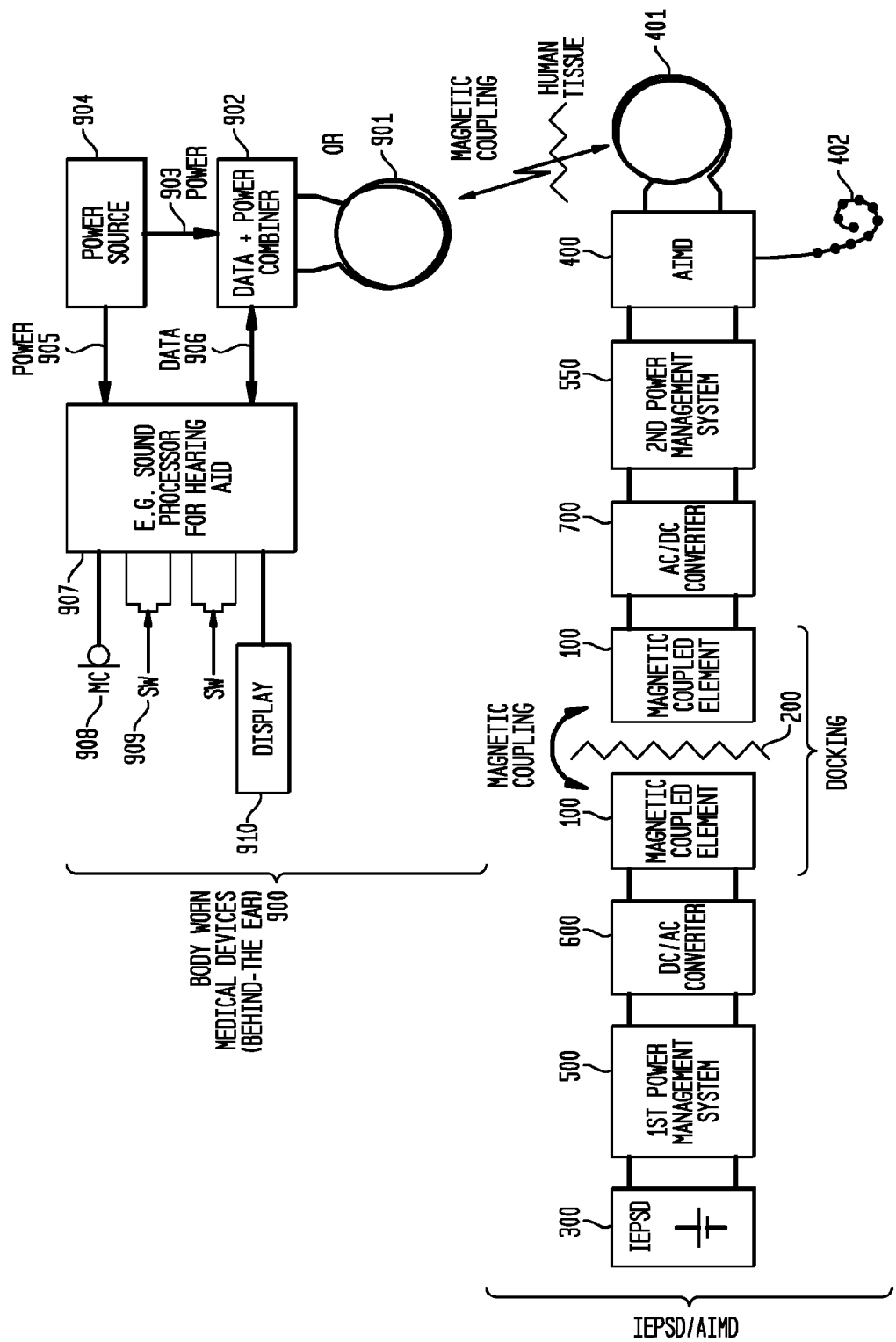
FIG. 6 is a schematic diagram of a partially implantable medical device having an implantable power source, in accordance with an embodiment of the present invention.

FIG. 6 illustrates an AIMD system wherein the IEPSD 300 can be recharged by an external power source 904 by magnetic coupling through coreless coils 401, 901, and then through magnetic coupled elements 100 having cored coils.

FIG. 6 illustrates a hearing system converting mainly acoustic airborne waves from a microphone system to stimuli signals applied to the cochlea by means of an electrode array 402. In this example, the body worn medical device 900 is a behind-the-ear device (BTE) including a microphone system 908, a sound processor with memory 907, a human user interface with control buttons 909 and a small display 910, a power source 904 such as Zn-Air batteries or a rechargeable Lithium-ion battery pack, and a combiner 902 for bidirectional data and power. The BTE 900 is coupled through an air coil 901, referred to as the headpiece coil, to the AIMD 400 by means of another air coil 401 belonging to the AIMD 400. This aspect is similar to the conventional air coil inductive link widely used for power transfer to cochlear implants. It is related to the arrangement disclosed in PCT application WO 2005/062668 by Cochlear Limited, the disclosure of which is hereby incorporated by reference.

It will be understood that the presently discussed embodiment is mainly concerned with the supply of power. Any compatible technique may be used to transfer data or signals to or from the implanted device. One alternative is an air coil approach at about 5 MHz, as is currently widely used. However, any suitable approach can be used. It is noted that the data requirements for a totally implanted device may be greatly reduced from a device requiring external input. It would be possible to have an arrangement where the magnetic field used for power transfer is modulated for bi-directional data transfer between AIMD 400 and IEPSD 300. The components of the IEPSD 300 and AIMD 400 may be as previously described. It is noted that the IEPSD 300 and AIMD 400 are preferably docked, and that when the body worn device 900 is connected, some power may be transferred from the AIMD 400 to the IEPSD 300 for later use, when the body worn device 900 is no longer in place.

Figure 7:
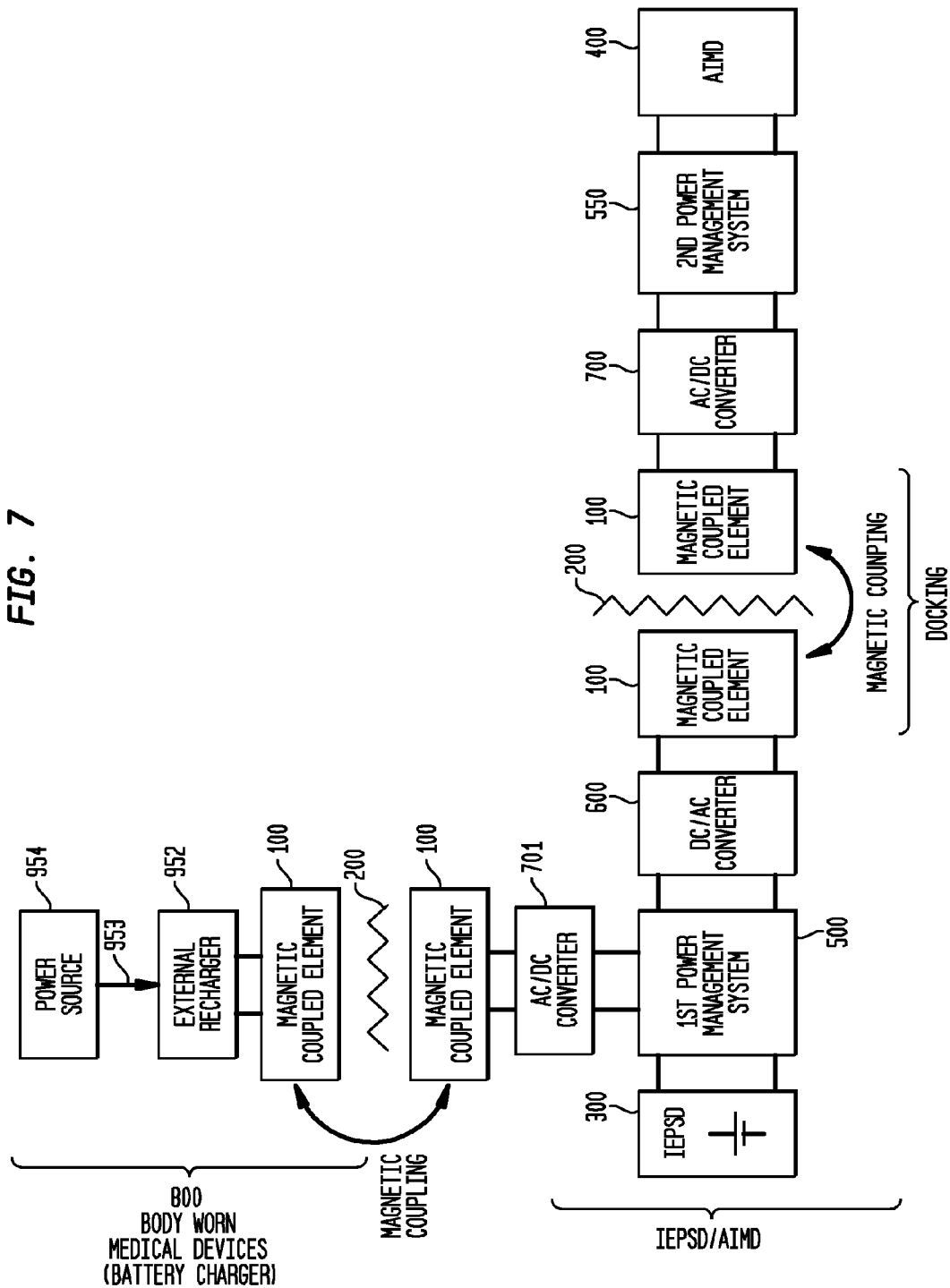
FIG. 7 is a schematic diagram of a fully implantable medical device having an implantable power source, in accordance with an embodiment of the present invention.

FIG. 7 illustrates a fully implantable medical system powered from an IEPSD 300 by magnetic coupled elements 100. The body-worn recharger 800 includes a power source 954, which may be a battery or mains power, coupled via an external recharger 952 to a magnetic coupled element 100. The magnetic coupled element 100 includes a magnetic permeable core, intended to pass power transcutaneously when required, for relatively short periods of the day. For most of the operation of the device, the AIMD 400 is powered from the IEPSD 300 without the need for an external power supply, thereby facilitating a fully implantable arrangement. Of course, it may be that in some cases certain components may not be implanted for operational reasons, for example, the microphone for an implantable hearing aid.

Figure 8:
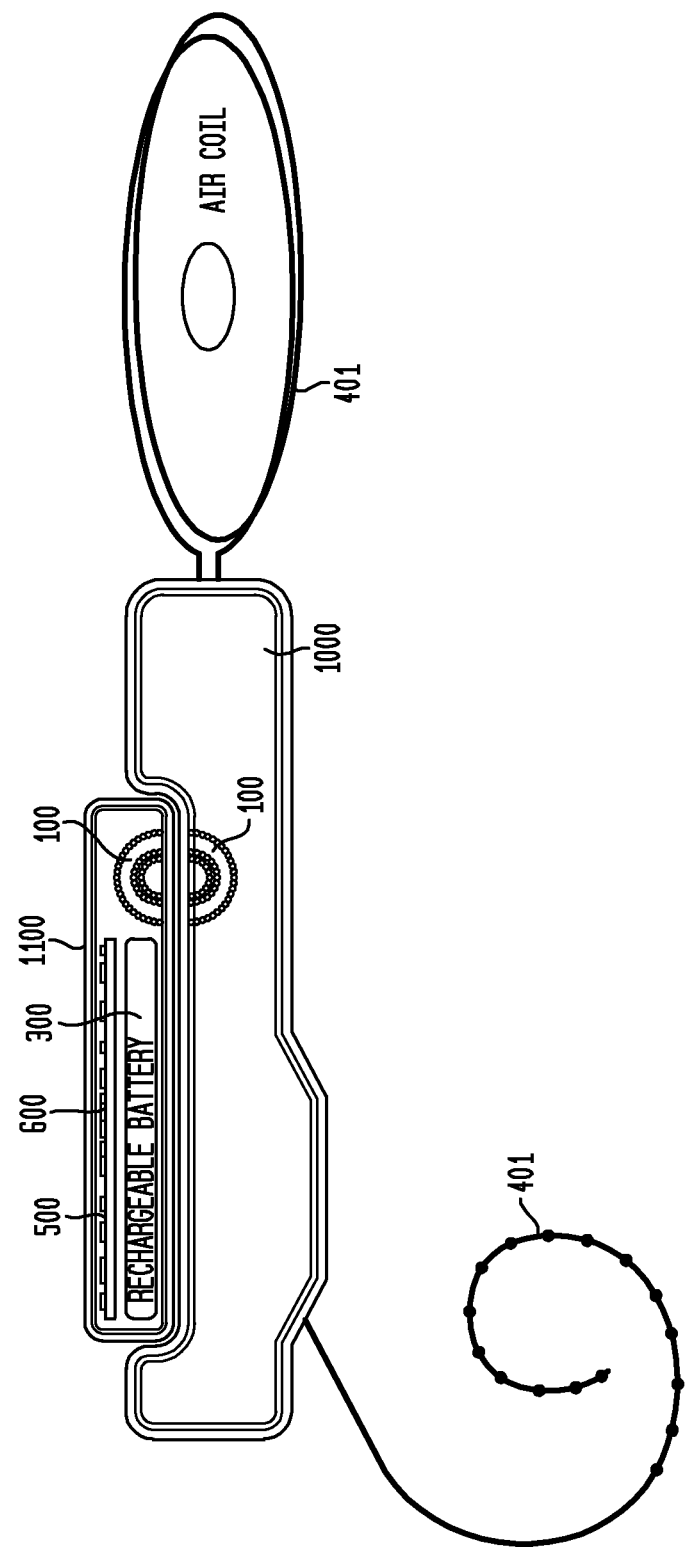
FIG. 8 is a partial cross-sectional view of an implantable medical device, in accordance with an embodiment of the present invention.

FIG. 8 shows an IEPSD unit 1100 which is adapted to dock with an AIMD unit 1000, in the illustrative case a cochlear implant. Electrical coupling between the devices is accomplished using a C-shaped core 100. It will be appreciated that this arrangement embodies a similar concept to that illustrated in FIG. 6.

Figure 9:
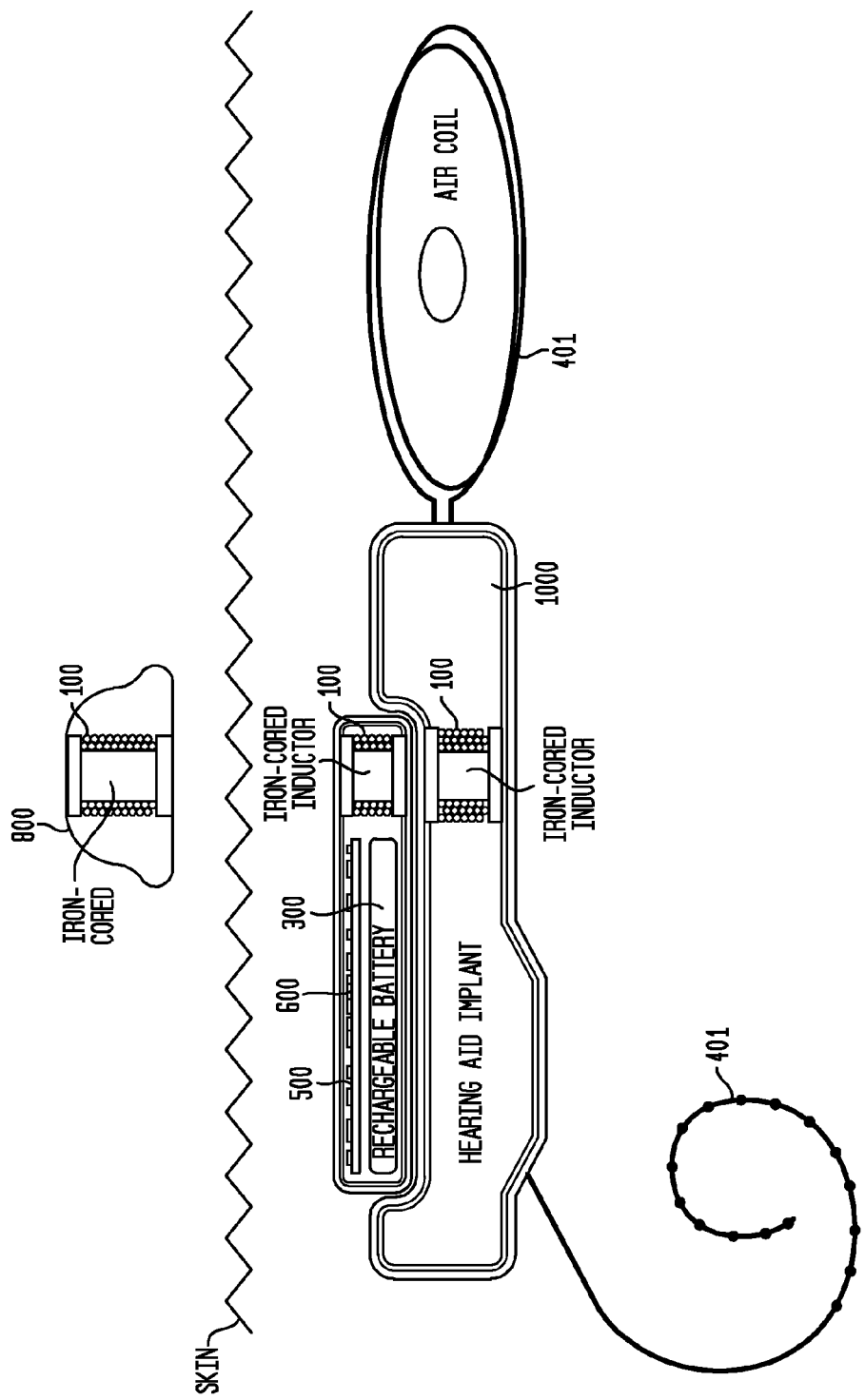
FIG. 9 is a partial cross-sectional view of an implantable medical device, in accordance with an embodiment of the present invention.

FIG. 9 shows a device similar to FIG. 8, but using a specific body worn power transfer arrangement 800 to recharge the IEPSD unit 1100. The air coil 401 can still be used to transfer data, or even power if required. In a similar arrangement, the air coil 401 could be omitted for a fully implantable device. FIG. 9 can be considered a practical embodiment based on the arrangement in FIG. 7.

Figure 10:
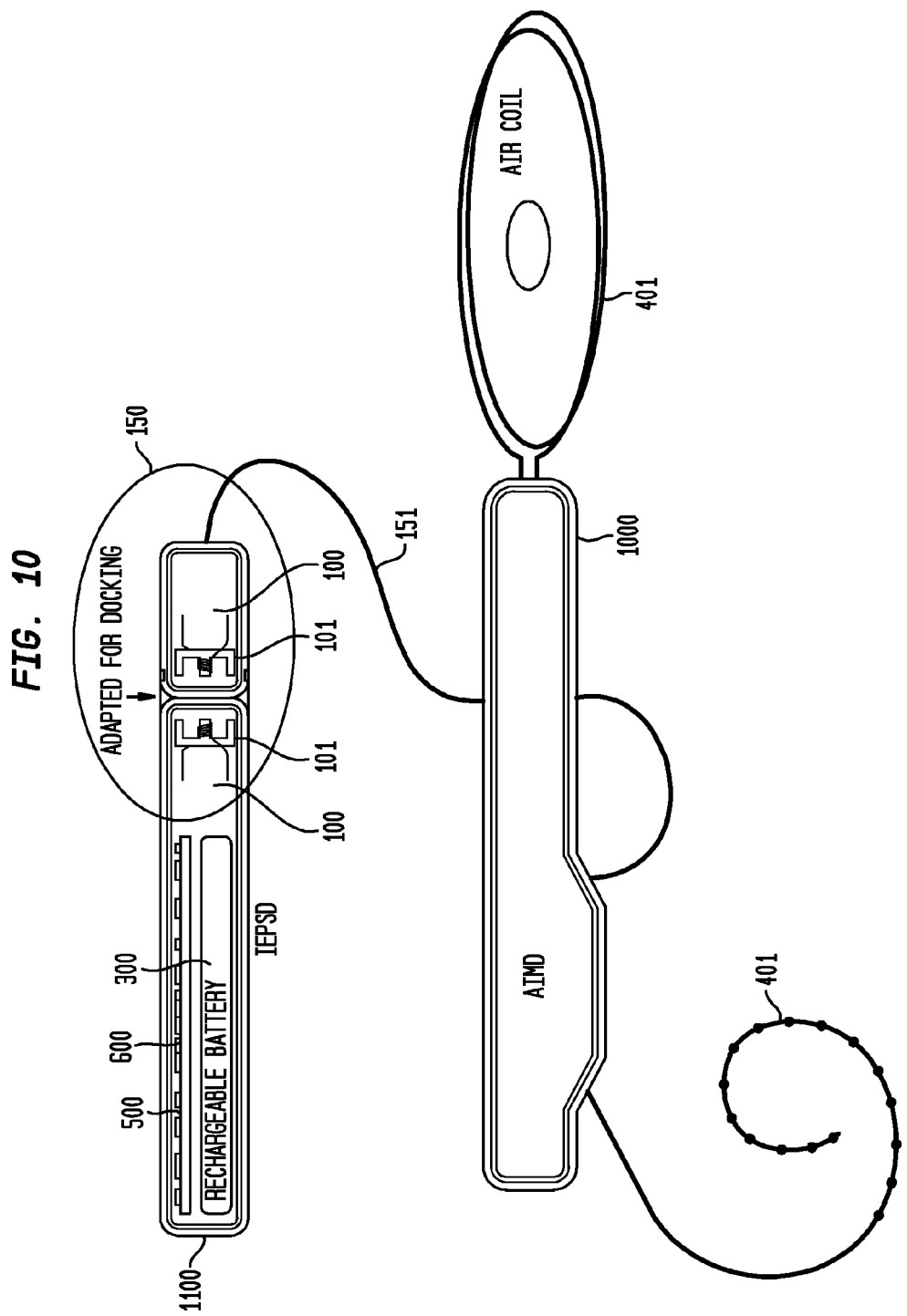
FIG. 10 is a partial cross-sectional view of an implantable medical device, in accordance with an embodiment of the present invention.

FIG. 10 shows a similar system, but where the AIMD unit 1000 has a cable extension 151 with connector system 150. In this case, the IEPSD unit 1100 can be located more remotely from the AIMD unit 1000, however, the same magnetically coupled power transfer arrangement 100 is used.

Figure 11:
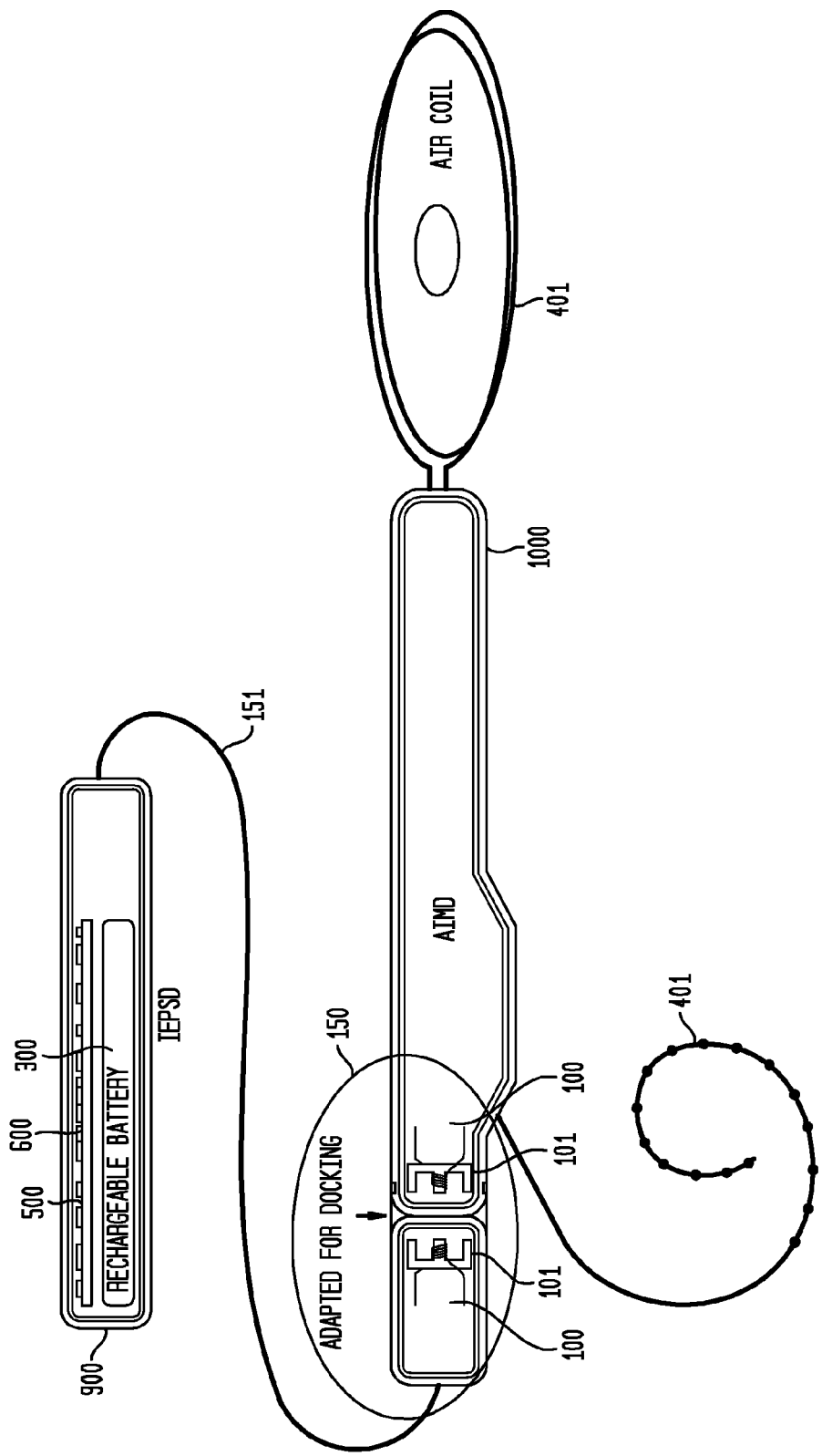
FIG. 11 is a partial cross-sectional view of an implantable medical device, in accordance with an embodiment of the present invention.

FIG. 11 illustrates a similar arrangement, but where the cable 151 extends from the IEPSD unit 1100 and the docking 150 occurs at the AIMD unit 1000.

Figure 12:
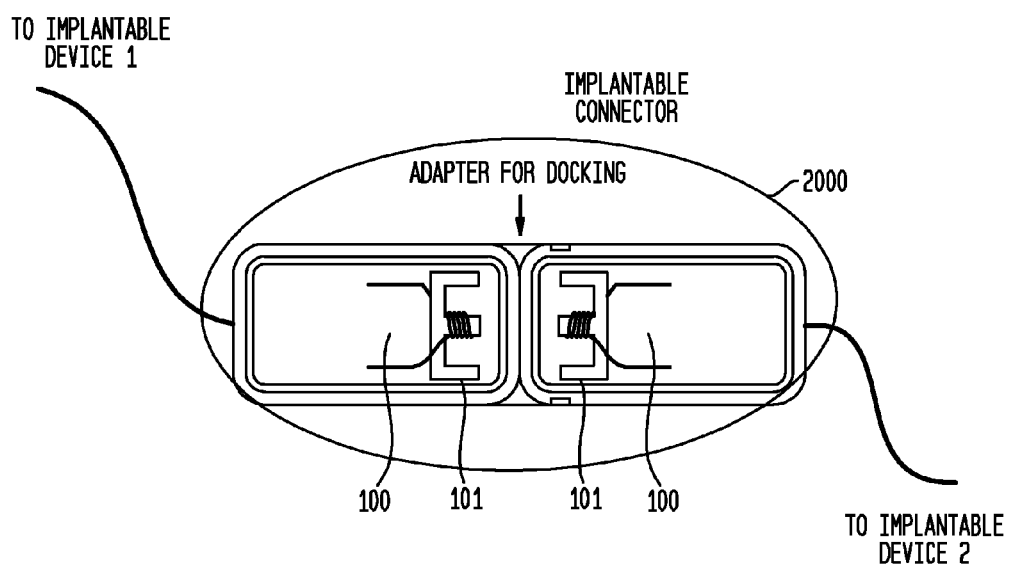
FIG. 12 is a cross-sectional view of a connector, in accordance with an embodiment of the present invention.

FIG. 12 illustrates an implantable connector system 2000, connecting two implantable devices by a magnetically permeable core to effect power transfer or even data transfer. The connector system consists of two mechanically mating parts.

Figure 13:
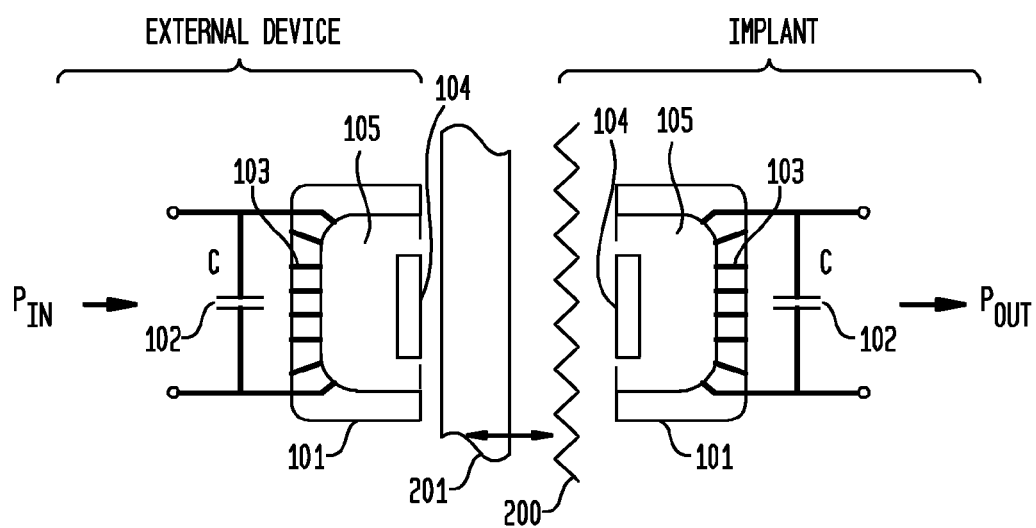
FIG. 13 illustrates a magnetically coupled element aligned using permanent magnets, in accordance with an embodiment of the present invention.

Embodiments of the present invention may also be implemented with mechanical snap or permanent magnets to align the magnetically coupled elements for optimal coupling. FIG. 13 illustrates an embodiment which uses permanent magnets 104 for aligning the external device and the implant. In this embodiment the magnetic coupled elements has a U-shaped configuration similar to the construction shown in FIG. 2C and further include permanent magnets 104. The magnets 104 act to locate and align their respective elements with each other across the casing 200 and skin/tissue 201. To avoid core saturation and drop in efficiency of the magnetic coupling, the magnets 104 are preferably separated from the U-shaped core 131 by an air gap or non-magnetic material 105.

It will be appreciated that data is also able to be transferred between the magnetically coupled elements of the present embodiment. Data may be transferred in conjunction power transfer or as a standalone transmission across the magnetically coupled elements.

It will be appreciated that there are many possible implementations of the present invention, and that variations and additions are possible within the general inventive concept. Many structural and functional equivalents are available, as will be apparent to those skilled in the art.

The invention claimed is:

1. An implantable medical device system, comprising:
   implantable first and second inductively coupled elements each comprising an inductive coil disposed about a magnetically permeable core;
   a first hermetically sealed casing that is at least partially electrically-conductive, wherein the casing is formed from a non-magnetic, low electrical conductive material relative to the core; and
   wherein the first element is disposed in the casing, and the second element is disposed external to the casing, and wherein the first and second elements are operable to transfer power across the at least partially conductive casing.

2. The implantable device system of claim 1, wherein the first and second elements are operable at a relatively low frequency in transferring power across the casing.

3. The implantable medical device system of claim 1, wherein the first casing is made from titanium or an alloy thereof.

4. The implantable medical device system of claim 1, wherein the first casing is a casing for an active implantable medical device, and wherein the system further comprises:
   an implantable power supply device comprising a second casing; and
   wherein the second element is disposed in the second casing.

5. The implantable medical device system of claim 4, wherein the active implantable medical device and the implantable power supply device are operatively and mechanically connected.

6. The implantable medical device system of claim 5, wherein at least one of the inductive coils is connected to the active implantable medical device or the implantable power supply device by a cable.

7. The implantable medical device system of claim 4, wherein the implantable: power supply device comprises a battery.

8. The implantable medical device system of claim 4, wherein the active implantable medical device is a cochlear implant.

9. The implantable medical device system of claim 1, wherein the first and second conductive elements each comprises at least one capacitor.

10. The implantable medical device system of claim 1, wherein the magnetically permeable core is formed from a ferrimagnetic material.

11. The implantable medical device system of claim 10, wherein the ferrimagnetic material is ferrite.

12. A power transfer system for an implantable device system having a first hermetically sealed casing that is at least partially electrically-conductive, the power transfer system comprising:
   implantable first and second inductively coupled elements each comprising an inductive coil disposed about a magnetically permeable core,
   wherein the first element is disposed in the casing, and the second element is disposed external to the casing, and wherein the first and second elements provide transfer of power across the at least partially conductive casing, and
   wherein the first casing is formed from a non-magnetic, low electrical conductive material relative to the core.

13. The system of claim 12, wherein the first casing is formed from titanium or an alloy thereof.

14. The system according to claim 12, wherein the first casing is formed from more than one different non-magnetic relatively low electrical conductive materials.

15. The system of claim 12, wherein the first and second conductive elements each comprise at least one capacitor.

16. The system of claim 12, wherein the magnetically permeable core is formed from a ferrimagnetic material.

17. The system of claim 16, wherein the ferrimagnetic material is ferrite.

18. An implantable device, comprising:
   a hermetically sealed casing that is at least partially electrically-conductive, wherein the casing is formed from a non-magnetic, low electrical conductive material relative to the core;
   an implantable first element configured to inductively couple with an implantable second element, wherein each of the first and second element comprise an inductive coil disposed about a magnetically permeable core, wherein the first element is disposed in the casing, and the second element is disposed external to the casing, and wherein the first element is configured to inductively couple with the second element to provide transfer of power across the at least partially conductive casing.

19. The implantable device of claim 18, wherein the first element is configured to operate with the second element at a relatively low frequency in transferring power across the casing.

20. The implantable device of claim 18, wherein the first casing is made from titanium or an alloy thereof.

21. The implantable medical device of claim 20, wherein the ferrimagnetic material is ferrite.

22. The implantable device of claim 18, wherein the device is an active implantable medical device.

23. The implantable device of claim 22, wherein the device is a cochlear implant.

24. The implantable device of claim 18, wherein the device is an implantable power supply device.

25. The implantable medical device of claim 18, wherein the first and second conductive elements each comprises at least one capacitor.

26. The implantable medical device of claim 18, wherein the magnetically permeable core is formed from a ferrimagnetic material.

* * * * *